United States Patent [19]

Guerra

[11] 4,186,740

[45] Feb. 5, 1980

[54] METHOD AND APPARATUS FOR REGULATING INTRAVENOUS FLOW OF A LIQUID

[76] Inventor: Romeo E. Guerra, 6118 Walnut Hill La., Dallas, Tex. 75230

[21] Appl. No.: 875,455

[22] Filed: Feb. 6, 1978

[51] Int. Cl.$^2$ .............................................. A61M 5/00
[52] U.S. Cl. ........................... 128/214 R; 128/214.2; 137/188; 137/403
[58] Field of Search .......... 128/214 R, 214 C, 214 E, 128/214.2, 227, DIG. 13; 222/52; 137/188, 403, 510

[56] References Cited

U.S. PATENT DOCUMENTS

| 2,907,340 | 10/1959 | Kenney | 137/510 X |
|---|---|---|---|
| 3,204,633 | 9/1965 | Hofstra | 128/214 E |
| 3,228,397 | 1/1966 | Moss | 128/214 E |
| 3,469,574 | 9/1969 | Durkan | 128/214 E |
| 3,469,582 | 9/1969 | Jackson | 137/510 X |
| 3,939,832 | 2/1976 | Miller | 128/214 R |
| 3,986,956 | 10/1976 | Anno | 128/214 E |
| 4,043,332 | 8/1977 | Metcalf | 128/214 E |
| 4,146,028 | 3/1979 | LeFevre | 128/214 R |

FOREIGN PATENT DOCUMENTS 342358 10/1921 Fed. Rep. of Germany ............ 128/272

Primary Examiner—Dalton L. Truluck
Attorney, Agent, or Firm—Charles W. McHugh

[57] ABSTRACT

An intravenous apparatus for administering liquids to a patient, including an elongated supply tube having a first end which is adapted to be connected to a reservoir of liquid. A flow-regulating device is attached to the remote end of the supply tube. A control tube having a length approximately the same as the supply tube is adapted to hang alongside the supply tube. Within the flow-regulating device is a flexible member such as a tube, bladder or diaphragm—with liquid that is being furnished by the supply tube passing interiorly of said flexible member, and there being some means for externally pressurizing said flexible member. A preferred means for pressurizing the flexible member is a column of liquid maintained in the control tube, with the control liquid having the same specific gravity as that of the supply liquid. A check valve is provided so that liquid may temporarily pass out of the supply tube and into the control tube, until a desired height of liquid has been achieved in the control tube. When the flow-regulating device is located very near a needle which is inserted into a patient's arm or leg, ordinary movement of that arm or leg will not change the rate of flow—because the height of liquid (i.e., head) changes simultaneously in both tubes. The flow-regulating device may be quite small, with a typical bladder or tube being about one inch long, and a rigid housing for said bladder being only slightly longer.

2 Claims, 12 Drawing Figures

METHOD AND APPARATUS FOR REGULATING INTRAVENOUS FLOW OF A LIQUID

This invention relates generally to the parenteral administration of liquids, and more particularly to an intravenous apparatus and method for administering liquids to a patient.

In the medical field, it is well known to employ various apparatus to control the introduction of liquids (such as whole blood, liquid plasma, saline solutions, or liquid nutrients) directly into a patient's veins. A typical intravenous (IV) liquid injection system includes: a bottle or other reservoir of liquid supported in an inverted position above the patient; a feed tube connected in some way to an opening in the bottom of the inverted bottle; a needle connected to the other end of the tube; and a valve mechanism for controlling the rate at which liquid is allowed to leave the bottle. A transparent drip chamber is ordinarily interposed between the bottle and the feed tube, so that a nurse or other attendant can observe the rate at which the liquid is dropping out of the bottle. A pool of liquid is also maintained in the lower portion of the drip chamber—under normal circumstances, to insure that no air enters the feed tube; in this way, air is precluded from being admitted to a patient's veins.

There have been numerous ways proposed from time to time for regulating the flow of liquid from an IV bottle. For example, manual flow control devices in the form of clamps or the like have been widely used, including those shown in U.S. Pat Nos. 3,099,429 to Broman and 3,167,085 to Redmer. Regrettably, mechanical devices wherein a section of IV tubing is squeezed in order to restrict the flow of liquid therethrough are not 100% reliable over a long period of time because of the inherent yielding or creep properties of the plastic tubing. That is, a suitable adjustment of a mechanical clamp to produce a certain flow rate at a given time will almost always produce a different flow rate after several minutes have passed, because of the tendency of the PVC tubing to "cold flow". In view of the notorious difficulties with mechanical clamps, it has been suggested that flow control be accomplished with an electrically operated apparatus such as that shown in U.S. Pat. No. 4,038,981 to LeFevre and Thomas. An additional suggestion for a flow regulator employing hydraulic techniques is found in U.S. Pat. No. 3,963,024 to Foldowsky.

While there have been many suggestions in the prior art for solving the inherent problem of cold flow in IV tubing, a much more severe problem arises if the pool of liquid in the bottom of the drip chamber is ever consumed—and the liquid that fills the IV tubing is also consumed. If an air bubble should ever be admitted to a patient's vein, the complications can be almost immediate and severe—and death of the patient would not be unexpected. For this reason, any time that an IV liquid is being administered to a patient, that patient should have very close attention by a nurse or other skilled person, in order to guard against accidental depletion of all of the liquid in an IV system. There is always the possibility, however, that a nurse may be called away to render emergency treatment to a second patient while an IV liquid is being administered to a first patient. If the nurse should be delayed in returning to the first patient, it would be desirable for the IV apparatus to have built-in properties so that it automatically terminated the flow of liquid when the bottle became empty. Accordingly, it is an object of this invention to provide an intravenous apparatus which terminates the flow of IV liquid to a patient when the bottle is completely drained.

It is another object to provide a mechanically simple and reliable technique for regulating the flow of IV liquids to a patient.

Still another object is to provide an IV flow regulation device which is insensitive to the elevation of the needle which is typically inserted into a patient's vein, such that a patient may raise his arm or leg (as the case may be) without interfering with the rate at which IV liquids are admitted to his body.

Still another object is to provide a hydraulically controlled system for regulating the flow of IV liquids, wherein the typical deficiencies of mechanical systems are eliminated, and electrical systems (which are dependent on a steady supply of electrical current) are also avoided.

These and other objects will be apparent from a study of the specification and claims appended hereto, and from reference to the attached drawing in which FIG. 1 is a perspective view of an intravenous feeding apparatus, showing a conventional drip chamber which is adapted to be inserted into the bottom of a bag or bottle of liquid, and also showing the new flow-regulating device;

In brief, the invention comprises an IV apparatus which includes an elongated IV supply tube having a first end which is connected to a reservoir of IV liquid in a typical manner, as through a drip chamber. Additionally, there is provided a control tube having a length which is approximately the same as that of the supply tube. Preferably, the control tube is of the same type of material as the IV supply tube, and it is similarly maintained in a sterile condition. The flow regulating device constitutes a rigid housing having a first, liquid-tight compartment with entrance and exit apertures, and the entrance aperture being connected with the second end of the supply tube. The exit aperture of the rigid housing is adapted for connection (through a short tube or the like) with a needle which is to be inserted into one of a patient's veins. The rigid housing also has a second compartment which is immediately adjacent the first compartment; and there is a flexible wall in common between the first and second compartments. The flexible wall or diaphragm is sufficiently pliable, and it is of such a size and shape, that it may essentially block off communication between the entrance and exit apertures of the first compartment. The second compartment is connected with the control tube, such that a liquid in the control tube can pressurize the second compartment, thereby affecting the amount by which the flexible wall is distended, which in turn regulates the flow of liquid between the entrance and exit apertures of the first compartment. In one embodiment a one-way check valve is provided between the first and second compartments in the rigid housing, such that a small portion of the IV liquid supplied from the reservoir is diverted to the control tube, where is subsequently acts to regulate the flow of the remainder of the IV liquid to the patient. The entire system is capable of being reliably sterilized and packaged in a sterile environment, and it is economical enough to be discarded after a single use.

Figure 1:
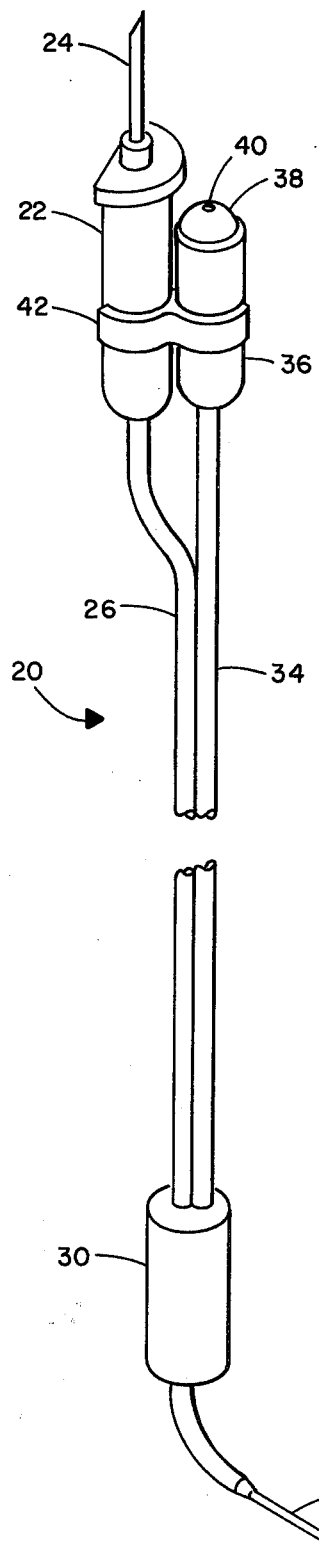

Referring particularly now to FIG. 1, an apparatus 20 according to the invention includes a conventional drip chamber 22 which is adapted to be inserted into the bottom of a reservoir of IV liquid in a known manner, as through piercing the reservoir with needle 24. Attached to the bottom of the drip chamber 22 is an elongated supply tube 26 having first and second ends. The second or lower end of the supply tube 26 is connected to the flow regulator 30, which may be positioned quite some distance away from the drip chamber 22. Indeed, the flow regulator 30 will typically be installed very close to the needle 32 which is to be inserted through the skin of a patient. One advantage of placing the automatic flow regulator 30 near the needle 32 is to eliminate any impact on feeding rates that might be introduced through changing the elevation of the needle 32. That is, if the needle is stuck in a patient's arm, it is desirable that the flow rate through the regulator 30 be the same at all times, regardless of whether the patient might have his arm raised or lowered. As will be explained more thoroughly hereinafter, the flow regulator 30 provides this beneficial property.

Figure 2:
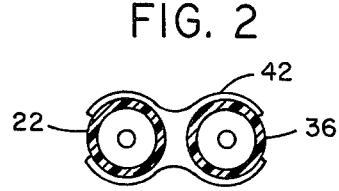
FIG. 2 is a cross-sectional veiw taken horizontally through the old drip chamber and a new flow-regulating bottle —as shown in FIG. 1.

In addition to the supply tube 26, a second elongated tube 34 is connected at one of its ends to regulator 30; its other, upper end is connected to what will be called a control bottle 36, which preferably is mounted (for convenience) alongside the drip chamber 22. The control bottle 36 may have a configuration very similar to one of the commercially available drip chambers, and may even be fabricated by eliminating the top of a conventional drip chamber and replacing it with a cap 38 having an aperture 40 therein. In such a case, the drip chamber 22 and control bottle 36 may be conveniently held in position by a plastic clamp 42, shown in FIG. 2.

Figure 3:
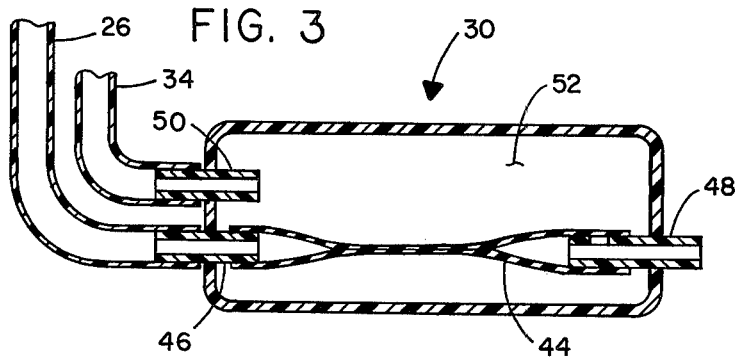
FIG. 3 is a somewhat schematic showing of a flow regulator of the type indicated generally in FIG. 1, with said regulator being illustrated in a dry condition prior to connection with an IV bottle.

Turning next to FIG. 3, the regulating means 30 includes a flexible member 44 installed within a rigid housing, which member is preferably in the form of a specially molded rubber tube. The flexible member 44 is serially connected with the supply tube 26 through a short piece of tubing 46. The downstream end of the flexible member 44 is adapted to be connected to the needle through the stub tube 48 and other appropriate tubing. The control tube 34 is connected to the interior of the regulator 30 through stub tube 50, so that it is in communication with the exterior of flexible member 44. Also, it will be noted that the stub tubes 46, 48 are separated by a sufficient distance so that the flexible tube 44 may be completely closed (squeezed together) if the chamber 52 is sufficiently pressurized. That is, the rigid housing of regulator 30 may be deemed to have two liquid-tight compartments, with the interior of tube 44 constituting a first compartment and the region around tube 44 constituting a second compartment which is immediately adjacent the first compartment. Examined in this way, the circumferential wall of flexible tubing 44 may be considered to be equivalent to a flow-control diaphragm between the first and second compartments. Of course, to be effective in accordance with this invention, the tubing or diaphragm must be sufficiently flexible and be so positioned as to be able to affect the flow of liquid between the entrance and exit apertures represented by tubes 46, 48.

Figure 4:
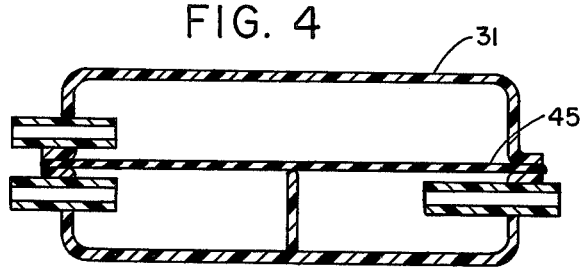
FIG. 4 is a cross-sectional, elevational view of an alternate embodiment of a flow regulator, wherein a diaphragm which bears against an elevated ridge replaces the flexible tube shown in FIG. 3.

An alternate embodiment of a flow control device is shown in FIG. 4, wherein a rigid housing 31 is divided into first and second compartments by a flexible diaphragm 45 which is sealed all around its periphery to the housing 31. In this embodiment, also, there is an entrance and exit aperture for the lower compartment through which IV liquids flow to the needle. As in the first embodiment, the passage of liquid through the lower compartment is regulated by adjusting the fluidic pressure in the upper compartment—and this is most conveniently accomplished by adjusting the height of a column of liquid in communication with said upper compartment.

Figure 5:
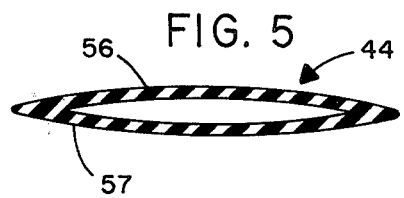
FIG. 5 is a cross-sectional, transverse view of a flexible tube which is serviceable in an embodiment like that shown in FIG. 3.
Figure 6:
FIG. 6 is a cross-sectional, transverse view of a mandrel upon which a flexible rubber tube (such as that shown in FIG. 5) might be cast.
Figure 7:
FIG. 7 is an illustration of what happens when a cylindrical tube is squeezed together, showing the small gaps that typically remain at the edges of the tube.

Turning next to FIG. 5, which is a transverse, cross sectional view of a preferred tubing member 44, it will be seen that the member includes what may be denominated as a top wall 56 and a bottom wall 57, with said walls being joined at their respective ends to form a continuous loop. Preferably, a member like that shown in FIG. 5 is made of relatively pure latex rubber having a thickness of only about 2 to 4 mils. Such material is similar to that typically employed in surgeon's gloves, and may be obtained from manufacturers who are skilled in providing sterilized rubber products for use in intravenous systems; one such source is Schmid Laboratories, Inc. of Little Falls, New Jersey. The member 44 is preferably molded around a mandrel shown in cross section in FIG. 6 so that the respective "edges" of the pieces 56, 57 will be nearly tangent. To perhaps better appreciate the reason for this preferred construction, FIG. 7 has been provided to illustrate what might happen if a flexible but normally circular tube was to be squeezed with a significant amount of external pressure. In such a case the top and bottom "walls" could be readily forced together in the center of a tube like that shown in FIG. 7; but it would take literally a crushing amount of force to completely eliminate the small gaps which would tend to remain at the "edges" of the tubing. These small gaps, even though very small in size, could absolutely preclude the desired inequivocal control over the passage of liquid through such tubing; and, while the leakage might be so small as to be considered more of an oozing than a literal flow, it is preferred that even this miniscule amount of flow be inhibited—for most situations. On the other hand, if circumstances are such that a minute amount of leakage could perhaps be tolerated through gaps like those shown in FIG. 7, then the extra expense of special cast members 44 like the one shown in FIG. 5 could possibly be avoided—through use of more conventional tubing. The principles of this invention can be applied in essentially any embodiment where the thickness and flexibility of a bladder or tube is such that it can respond to the pressure differentials that are available—from those values which can be measured in fractions of an inch of water up to much larger pressures. While the flexible member 44 and all of the other components of the system will obviously have to be sterile if they are to be used for IV feeding, the exact composition of the flexible member is not critical. In fact, the principle upon which the invention is based was first tested using a rubber balloon which had been purchased in a toy store—said balloon being the most conveniently available material at the moment. And, as will surely be understood, the uniformity in wall thickness of a toy balloon is not usually its most appealing property. It should be apparent, then, that a wide range of tolerance may be accommodated in the tubing member 44.

Figure 8:
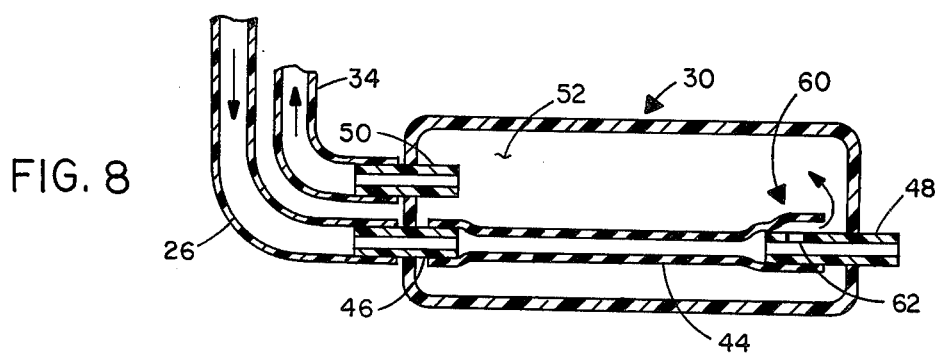
FIG. 8 is an illustration of the apparatus depicted in FIG. 3 and showing the flow-regulating device as it is being filled with liquid.
Figure 9:
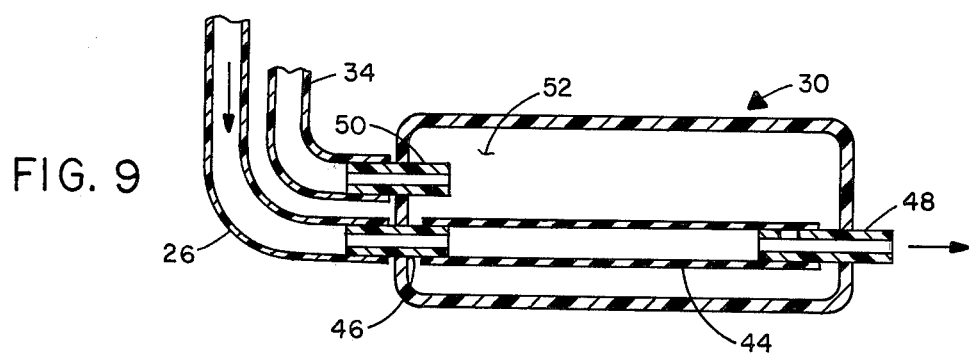
FIG. 9 is a showing of the apparatus depicted in FIG. 3 wherein the external and internal pressures on the flexible tube are balanced, and the IV liquid is passing to the needle in a patient.

Turning next to FIG. 8, another significant feature of the preferred embodiment of the invention is disclosed, namely, a one-way check valve which connects the first and second chambers of the flow regulator 30. The check valve 60 is shown in FIG. 8 in its open condition, which is realized when the regulator 30 is first placed in communication with the IV reservoir. The IV liquid will initially fill the supply tube 26, the flexible tube 44, and the tube 48, plus the closed needle. Air will be initially bled out of the system through an aperture 62 in tube 48, by forcing outward that small segment of flexible tube 44 which covers the aperture. In addition to bleeding air out of the first compartment, the check valve 60 also permits the IV liquid to pass into the second compartment 52 and the control tube 34 (but not vice versa). Eventually the IV liquid will rise into the control tube until it almost reaches the level of liquid in the supply tube; it will not reach the identical level of the supply tube because the resiliency of the tube 44 (in the region of the aperture 62) serves to counteract some of the pressure exerted by the column of liquid in the supply tube. To cause the IV liquid to rise higher in the control bottle 36, the operator will usually squeeze the flexible bottle gently, then place his finger over the aperture 40, and subsequently release the sqeezing pressure on the bottle. As the control bottle 36 returns to its original cylindrical configuration, a slight vacuum is created, causing additional IV liquid to be drawn out of the drip chamber 22 and through check valve 60. After the desired level of IV liquid is achieved in bottle 36, the operator would merely remove his finger from aperture 40, thereby restoring the bottle to atmoshperic pressure. Turning next to FIG. 9, let it be assumed that the user of the apparatus 20 has positioned the bottle 36 above the patient so that the level of liquid therein is essentially the same as the level of liquid in drip chamber 22. This is easily done using the clamp 42 by simply forcing the bottle 36 up or down against the biasing force of the cantilevered arms of the clamp. Having established an equilibrium condition between the two columns of liquid (in tubes 26, 34, respectively), any additional liquid dropped into drip chamber 22 will serve to pressurize member 44 internally; and, with the needle having been opened, a balanced flow condition can be realized—such as that shown in FIG. 9. Thus, in a routine "open flow" condition, the hydraulic pressure on both sides of the flexible tube 44 will be balanced, and flow of IV liquid out of the needle will be primarily dependent upon orifice sizes or restrictions other than member 44.

Perhaps it would be appropriate at this time to note that there is an advantage in using the same type of IV liquid which is being administered to the patient as the control liquid—because the specific gravity of the liquid in both of the tubes 26, 34 and both of the chambers in regulator 30 will be the same. Hence, the hydraulic head of the liquid in both sides of the system will be the same when the column heights are the same. The amount of IV liquid which could be categorized as "wasted" by virtue of its dedication to a control function would normally be very small, e.g., on the order of only a few cc's of liquid—even if the tube 34 is a typical five feet in length. However, if it should be desired to use another control liquid (such as pure water), this would be possible—as long as there is no way for the control liquid to enter the supply line.

Figure 10:
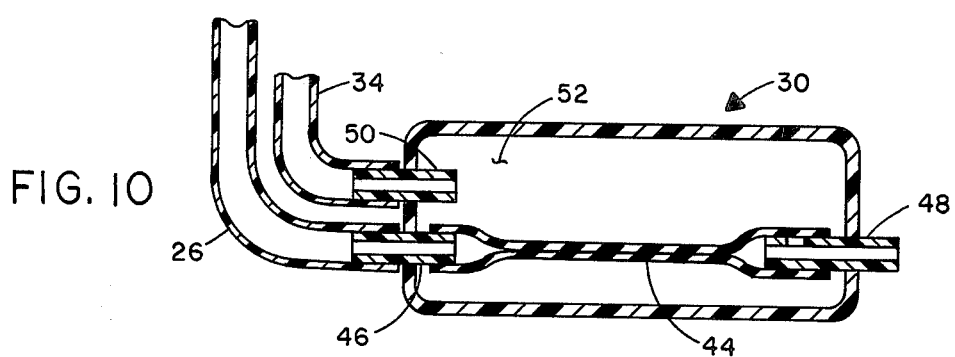
FIG. 10 is another showing of the apparatus of FIG. 3 wherein the pressure of fluid in the source tube has dropped appreciably below the pressure in the control tube, and the flexible member has been collapsed, shutting off flow of IV liquid to the needle.

Referring next to FIG. 10, let it be assumed that all of the IV liquid has been drained from the reservoir, so that the level of liquid in the drip chamber has started to fall. This will happen because liquid will still flow out of the drip chamber 22 even though no new liquid is coming in. In due time, the level of IV liquid will fall sufficiently so that the hydraulic pressure within flexible tube 44 is significantly lower than the external pressure exerted by the stable column of liquid in control tube 34. In such a case, illustrated in FIG. 10, the regulator tube 44 will be tightly squeezed together, and flow to the needle through said tube will be interrupted. Using the materials and dimensions, etc., recommended herein, there will be essentially no flow of fresh liquid to the needle when the system is in a condition like that shown in FIG. 10, regardless of how long the apparatus is left in that condition. One reason this is so is that the apparatus 20 is essentially self-enforcing in its off condition; and, any minute leakage of liquid through tube 44 to the needle would only serve to lower the height of liquid in tube 26—thereby increasing the differential between internal and external pressures on tube 44, causing it to be squeezed even tighter by the hydraulic pressure in chamber 52. In fact, an exemplary unit has been left for days in a condition like that shown in FIG. 10, with no loss of liquid from the needle.

While the apparatus 20 is obviously capable of providing flow rates between the two extremes of "full open" shown in FIG. 9 and "full closed" shown in FIG. 10, it will perhaps also be informative to discuss the degree of control that is achievable between these two extreme conditions. With the preferred system described herein, flow rates as slow as one drop in a four hour period have been routinely maintained. Using the relationship of approximately 15 drops per cc of liquid, it should be appreciated that a very low dosage rate can be realized with the system described herein. Of course, increasing the thickness of the rubber material used in a bladder or tube 44 might offer some advantage with regard to strength of the material; but, the stronger the material, the less sensitive will be the member 44 to external pressure in compartment 52. Hence, it is preferred that the flexible material (of latex rubber or the like) have a thickness which is not much more than about 4 mils—as long as the member 44 is always subjected to an external control pressure which is greater than its internal pressure. That is, if the member 44 should ever be subjected to an internal pressure significantly greater than its external pressure, then—like a balloon—there is a potential risk that it might stretch to the point of bursting. But, as long as the external pressure is equal to or greater than the internal pressure, there is relatively little stress on a tube 44 which might cause it to rupture.

In use of the IV system 20, a nurse or hospital attendant would typically receive it from a supply room in a completely dry and sterile condition. She would then select the liquid which has been prescribed by a doctor and insert the needle 24 into the bottom of the bottle. The bottle will be at substantially atmospheric pressure, and will promptly begin to supply the IV liquid to the drip chamber 22. The elongated supply tube 26 will also begin to fill, as well as the flexible member 44. When the member 44 is about full, some of the liquid will begin to pass through aperture 62 into the second compartment 52 of the flow regulator. Of course, the communication between the interior of member 44 and compartment 52 is only temporary, and such communication ceases when an equilibrium condition has been achieved between the two compartments in regulator 30—such that the resiliency of the rubber material over aperture 62 causes said aperture to be tightly closed. When the needle is subsequently opened and placed in a patient's vein, the pressure in tube 48 drops to essentially zero (i.e., atmospheric pressure), and the hydraulic head in tube 34 insures that the aperture 62 will be sealingly closed. In effect, then, the check valve 60 as disclosed herein is maintained in a closed condition by two forces: the resilient force in the rubber member 44 which has been stretched over tube 48, and a pressure differential between compartment 52 and tube 48.

Figure 11A:
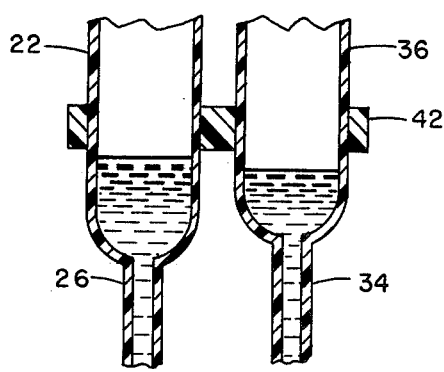
FIG. 11A is a diagrammatic showing of the respective liquid level heights which correspond to conditions depicted in FIG. 9.
Figure 11B:
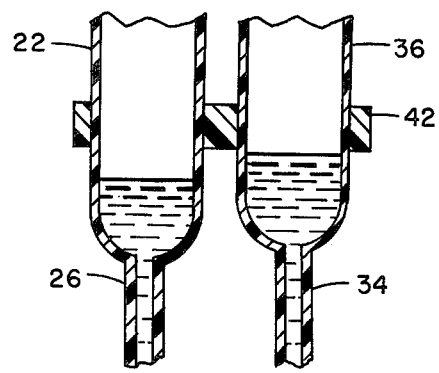
FIG. 11B is a diagrammatic view of conditions which could cause the flow regulator to halt flow of liquid, as shown in FIG. 10.

The desired flow rate out of needle 32 is subsequently established manually through the simple step of adjusting the height of control chamber 36 with respect to drip chamber 22. This is illustrated in FIGS. 11A and 11B, with the relationship shown in FIG. 11A being appropriate for permitting a relatively slow flow of liquid to the supply tube 26 and the condition shown in FIG. 11B being appropriate to essentially terminate flow to the supply tube and needle 32. The height difference depicted in FIG. 11B could have been realized by manually raising the chamber 36 until its liquid is above the level of liquid normally maintained in drip chamber 22; or, such a relationship would automatically be established if the reservoir of IV liquid was empty, such that no new liquid was being furnished to the drip chamber 22. That is, the level of liquid in chamber 36 cannot drop after it has once been established, so the drainage of liquid from drip chamber 22 soon creates the difference in column heights illustrated in FIG. 11B. Of course, a differential in liquid column heights of a quarter inch or so will not establish a very great pressure differential in regulator 30. (In fact, an inch of water will produce a pressure at the bottom of said tubing of about 0.036 psi, and a liquid heavier than water will typically produce only a slightly greater pressure.) But, a mere ¼ inch differential of column heights may be enough to shut down an IV system like that shown herein. It will be appreciated therefore, that the system 20 responds to a hydraulic pressure differential which may be accurately described as very small.

It should also be noted that the state of the IV bottle or reservoir is sensed hydraulically, in the same way that the supply of the IV liquid to tube 26 is being controlled hydraulically. In other words, the system described herein automatically tells itself that the IV bottle is empty (by sensing a falling liquid level in drip chamber 22), and then automatically operates to shut down the supply of fresh liquid to tube 26—both of these being accomplished hydraulically. And, it should be noted that the system is self-contained, requiring no external power source or controls. Hence, if it should ever become necessary to start the administration of an IV liquid at one place and then move the patient to a remote location, the system 20 disclosed herein is readily portable and can be easily moved with the patient.

A further advantage of the system disclosed herein is that the flow of liquid through regulator 30 is essentially immune to changes in the elevation of the regulator 30—because the heights of both the supply column and the control column change by an equal distance when the regulator 30 is moved. In accordance with this system, the regulator 30 can be affixed to the lower ends of the two tubes 26, 34, which are typically about five feet in length; the regulator is then connected to a needle 32 through a short length of tubing some two or three inches long. Then, if the needle is inserted into a vein in a patient's arm, it will not matter much whether the patient sits upright, lays down, rolls over, or otherwise moves his arm; the once-established flow rate will remain essentially the same. This may be referred to for convenience as the "dynamic" control which is available with the device 30—in contrast to the "static" control which is realized by adjusting the elevation of control chamber 36. Such dynamic control is not available with previously known systems which employ a mechanical clamp, because changing the length of a column of liquid between a prior art clamp and a needle will significantly change the pressure against which liquid is being supplied. In fact, it is not unusual in prior art systems for flow to be completely stopped if a patient elevates his arm, or increased to a rate substantially in excess of that established by a nurse if the needle should be lowered significantly below the elevation where the flow rate was set with a mechanical clamp. While it is not intended to suggest that the flow rates realized from the system disclosed herein would be totally immune to any possible change in column height, it is true that the flexible rubber bladder 44 is essentially immune to changes of at least 18 inches, which is about all that a patient might be expected to move an arm under conditions where IV feeding would likely be administered. In this regard, it is believed that the essentially linear cross section of the tube 44 is particularly important to contributing to the excellent control that is realized. Such a tube 44 having thin walls about ¼ inch wide which are approximately tangent where they join at their respective ends appears to offer an ideal amount of control. Too, the regulator 30 having such a tube 44 therein need not be bulky. In fact, a typical tube 44 would likely have a height of only about 1/64 inch; so a small rigid container of about two inches in length will normally be more than adequate to encompass a suitable tube 44.

While the preferred placement of the regulating device 30 in a system 20 has been described as being much closer to the needle 32 than the IV bottle, the relative location of a device such as that shown in FIG. 3 is not quite as significant if the device is merely being used as a shut-off valve, per se. That is, if a flow regulator 30 is not connected directly to a needle in a patient's vein, then its relative position with respect to the IV bottle is not so important. Perhaps this will be better appreciated when one considers that the length of tubing downstream of the regulator 30 shown in FIG. 1 holds essentially an unregulated column of liquid, and the pressure immediately downstream of the regulator will be essentially zero. If a long column of liquid existed between the regulator 30 and a patient's vein, the fall of this column of liquid as the vein absorbed more liquid would tend to create a vacuum within tube 48, which would then tend to collapse flexible tube 44—rendering the desired control function of tube 44 ineffective. On the other hand, if a device 30 is not connected directly to a vein on its downstream side, then the tendency to create a vacuum in tube 48 would not necessarily arise, and the flow-regulating properties of tube 44 would have utility based solely upon the up-stream conditions which affect the relative pressure between the two compartments in member 30.

One other characteristic of the apparatus described herein is perhaps worthy of mention, namely, its properties permit hospital personnel to replace a first IV bottle with any subsequent number of bottles without having to again adjust the flow regulator 30. That is, once the flow regulator 30 has been suitably adjusted to produce a desired dosage rate for a patient, the system 20 is totally immune to any changes in the supply source. Therefore, when the first bottle is empty, it may be replaced with a second and any subsequent number of bottles without requiring any new calibration by hospital personnel. Of course, this is in marked contrast to prior art systems where the substitution of one bottle for another always required a fresh adjustment of some valve—because prior art valves had to be turned completely off when a bottle was being changed.

While only certain preferred embodiments of the invention have been disclosed in great detail herein, it will be apparent to those skilled in the art that modifications thereof can be made without departing from the spirit of the invention. Thus, any specific structure shown herein is intended to be exemplary and is not meant to be limiting, except as described in the claims appended hereto.

What is claimed is:

1. A construction having utility in intravenous flow control, comprising:
    (a) a rigid housing having a first liquid-tight compartment with entrance and exit apertures, with the entrance aperture being adapted for connection with a reservoir of liquid which is to be fed intravenously to a patient, and the exit aperture being adapted for connection with a needle which is to be inserted into one of a patient's veins, and said housing having a second compartment which is immediately adjacent the first compartment, and there being a flexible diaphragm constituting a wall in common between said first and second compartments, and the diaphragm being sufficiently flexible and so positioned so as to selectively restrict the flow of liquid between the entrance and exit apertures of said first compartment; and
    (b) a one-way check valve positioned between the first and second compartments, such that liquid may pass from the first compartment into the second compartment but not vice versa.

2. The method of intravenous feeding of a person, comprising the steps of:
    (a) connecting a bottle for liquid at substantially atmospheric pressure to one of a person's veins through a drip chamber, an elongated supply tube and a needle; and
    (b) automatically terminating the supply of fresh liquid to the supply tube when the bottle is empty but maintaining in the supply tube such liquid as was supplied thereto before the bottle was emptied, such that the entrance of air into the person's vein is precluded, and wherein the terminating step involves regulating the flow of fresh liquid through the supply tube with a quantity of control liquid that was earlier obtained from said bottle, and stopping said flow when the pressure exerted by a column of fresh liquid in the supply tube is significantly less than the pressure exerted by a control column of control liquid which was previously obtained from the bottle.

* * * * *